(12) United States Patent
McCauley et al.

(10) Patent No.: US 11,148,987 B2
(45) Date of Patent: Oct. 19, 2021

(54) METHOD OF TREATING A NEUTRALIZED ARALKYL HYDROPEROXIDE CLEAVAGE STREAM

(71) Applicant: SHELL OIL COMPANY, Houston, TX (US)

(72) Inventors: Garry Morgan McCauley, Deer Park, TX (US); Jamie Jerrick Juliette, Deer Park, TX (US); David Randall Faske, Deer Park, TX (US); Thomas Robert Porter, Deer Park, TX (US)

(73) Assignee: SHELL OIL COMPANY, Houston, TX (US)

(*) Notice: Subject to any disclaimer, the term of this patent is extended or adjusted under 35 U.S.C. 154(b) by 0 days.

(21) Appl. No.: 16/640,615

(22) PCT Filed: Aug. 22, 2018

(86) PCT No.: PCT/US2018/047437
§ 371 (c)(1),
(2) Date: Feb. 20, 2020

(87) PCT Pub. No.: WO2019/040570
PCT Pub. Date: Feb. 28, 2019

(65) Prior Publication Data
US 2021/0130274 A1    May 6, 2021

Related U.S. Application Data

(60) Provisional application No. 62/549,021, filed on Aug. 23, 2017.

(51) Int. Cl.
*C07C 37/72* (2006.01)
*C07C 45/80* (2006.01)
*C07C 39/04* (2006.01)
*C07C 49/08* (2006.01)

(52) U.S. Cl.
CPC .............. *C07C 37/72* (2013.01); *C07C 45/80* (2013.01); *C07C 39/04* (2013.01); *C07C 49/08* (2013.01)

(58) Field of Classification Search
CPC ......... C07C 37/72; C07C 45/80; C07C 39/04; C07C 49/08
See application file for complete search history.

(56) References Cited

U.S. PATENT DOCUMENTS

| 4,262,150 A | 4/1981 | Pujado |
| 4,262,151 A | 4/1981 | Pujado |
| 6,825,387 B2 * | 11/2004 | Wilks ...................... C07C 37/08 568/754 |
| 6,965,056 B1 | 11/2005 | Taggart, II et al. |

OTHER PUBLICATIONS

International Search Report and Written Opinion received for PCT Patent Application No. PCT/US2018/047437, dated Oct. 26, 2018, 09 pages.

* cited by examiner

*Primary Examiner* — Sikarl A Witherspoon
(74) *Attorney, Agent, or Firm* — Shell Oil Company

(57) ABSTRACT

A method of reducing the salt content of a neutralized aralkyl hydroperoxide cleavage mass stream comprising passing the neutralized stream into a vessel, the vessel having an inlet, two outlets, an aqueous layer and a hydrocarbon layer wherein the neutralized stream enters the vessel through a first inlet and a hydrocarbon stream exits the vessel through a first outlet that is in fluid communication with the hydrocarbon layer.

22 Claims, 2 Drawing Sheets

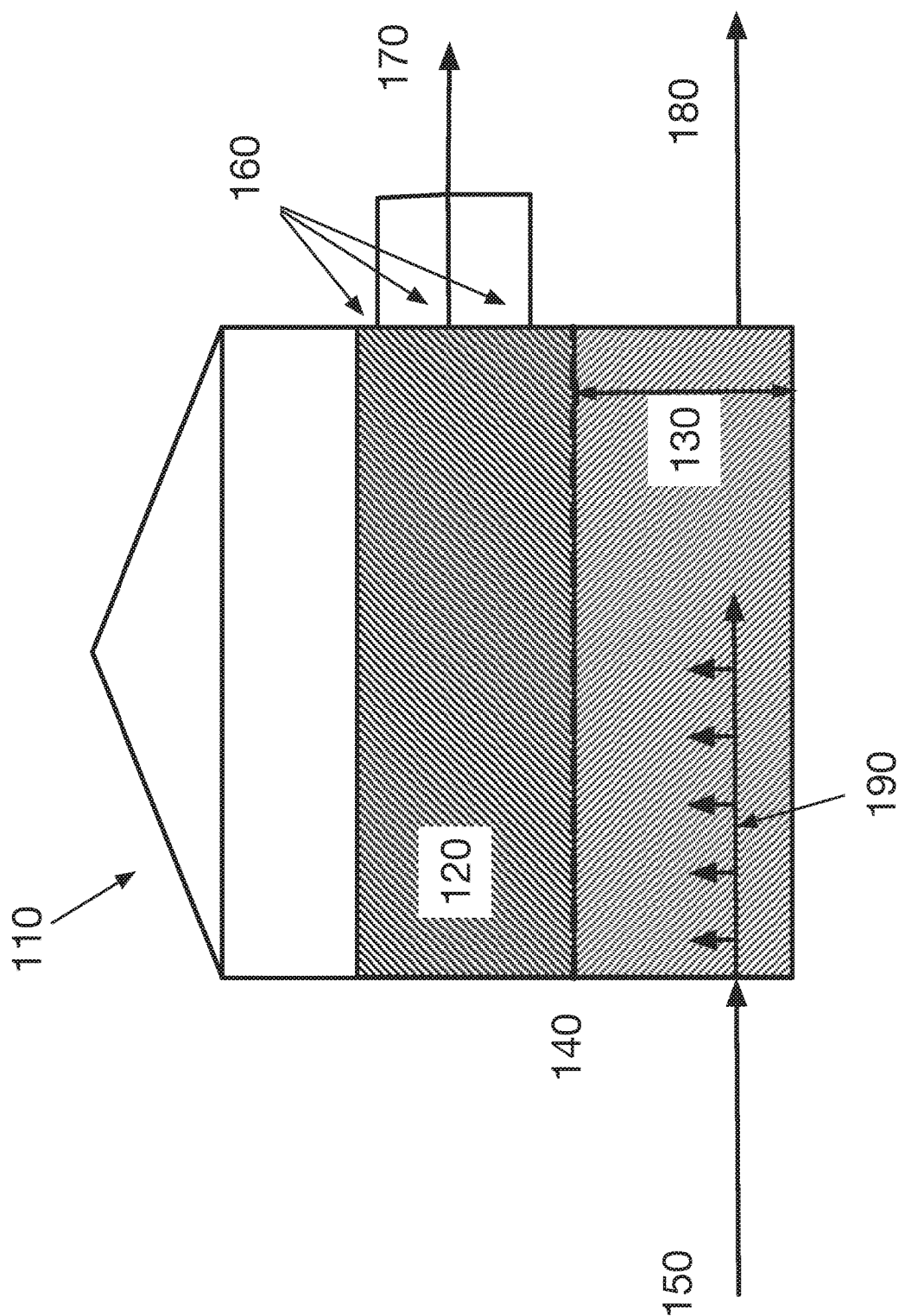

METHOD OF TREATING A NEUTRALIZED ARALKYL HYDROPEROXIDE CLEAVAGE STREAM

CROSS REFERENCE TO RELATED APPLICATIONS

This is a national stage application of International Application No. PCT/US2018/047437, filed 22 Aug. 2018, which claims benefit of priority to U.S. Provisional Patent Application No. 62/549,021, filed 23 Aug. 2017.

FIELD OF THE INVENTION

The invention relates to a method of treating a hydrocarbon stream produced as an intermediate in a phenol process.

BACKGROUND

Phenol is manufactured by oxidizing an alkyl substituted aromatic compound, such as cumene, to form the hydroperoxide derivative thereof, followed by cleavage of the hydroperoxide with a mineral acid such as sulfuric acid to form a cumene hydroperoxide cleavage mass. The cleavage mass generally contains species such as phenol, acetone, alpha-methyl styrene, cumene, cumyl phenol, dimethylbenzyl alcohol, acetophenone, alpha-methyl styrene dimers, tars, heavies and the mineral acid. Prior to separating out the different species and recovering phenol and acetone, the cleavage mass is neutralized with a caustic, such as sodium hydroxide, to prevent the acidic cleavage mass from causing corrosion in downstream equipment. The resulting salts from the neutralization are removed in a wash/phase separation step before feeding the at least partially neutralized cleavage mass to a crude purification column that produce an acetone rich top stream and a phenol rich bottom stream. The separated streams may be subjected to further purification steps. The at least partially neutralized cleavage mass may be stored in one or more tanks or surge vessels. Even after the wash an amount of salt remains in the cleavage mass and this quantity of salt will become more concentrated as the stream passes from one purification column to another.

One method for removing salts is described in U.S. Pat. No. 6,965,056 where the process comprises a) separating a neutralized aralkyl (aryl alkyl or alkyl aryl) hydroperoxide cleavage mass stream containing salts of neutralization into a crude ketone stream and a crude phenolic stream containing the salts of neutralization; b) separating the crude phenolic stream into a concentrated phenolic-rich stream, enriched in phenolic compounds, and a crude phenolic bottoms stream enriched in tars and alpha methyl styrene dimers, each compared to the crude phenolic stream, said crude phenolic bottoms stream containing salts of neutralization; c) to the crude phenolic bottoms stream, adding water and a diluent composition, thereby forming a phase separable crude phenolic bottoms stream, said diluent composition comprised of a hydrocarbon phase compatible with the crude phenolic bottoms stream and having a combined density lower than the density of the crude phenolic bottoms stream at separation temperatures; d) separating the separable crude phenolic bottoms stream into a hydrocarbon phase and an aqueous phase containing salts of neutralization; whereby the amount of salts of neutralization in the hydrocarbon phase is reduced compared to the amount of salts of neutralization present prior to separation.

It would be advantageous to develop an improved method of reducing neutralization salts to prevent problems in the downstream processing equipment.

SUMMARY OF THE INVENTION

The invention provides a method of reducing the salt content of a neutralized aralkyl hydroperoxide cleavage mass stream comprising passing the neutralized stream into a vessel, the vessel having an inlet, two outlets, an aqueous layer and a hydrocarbon layer wherein the neutralized stream enters the vessel through a first inlet and a hydrocarbon stream exits the vessel through a first outlet that is in fluid communication with the hydrocarbon layer.

The invention also provides a method of retrofitting a vessel used for storing an amount of a neutralized aralkyl hydroperoxide cleavage mass stream comprising adding an outlet at or near the top of the hydrocarbon layer.

BRIEF DESCRIPTION OF THE FIGURES

FIG. 2 depicts another embodiment of the invention.

DETAILED DESCRIPTION

Figure 1:
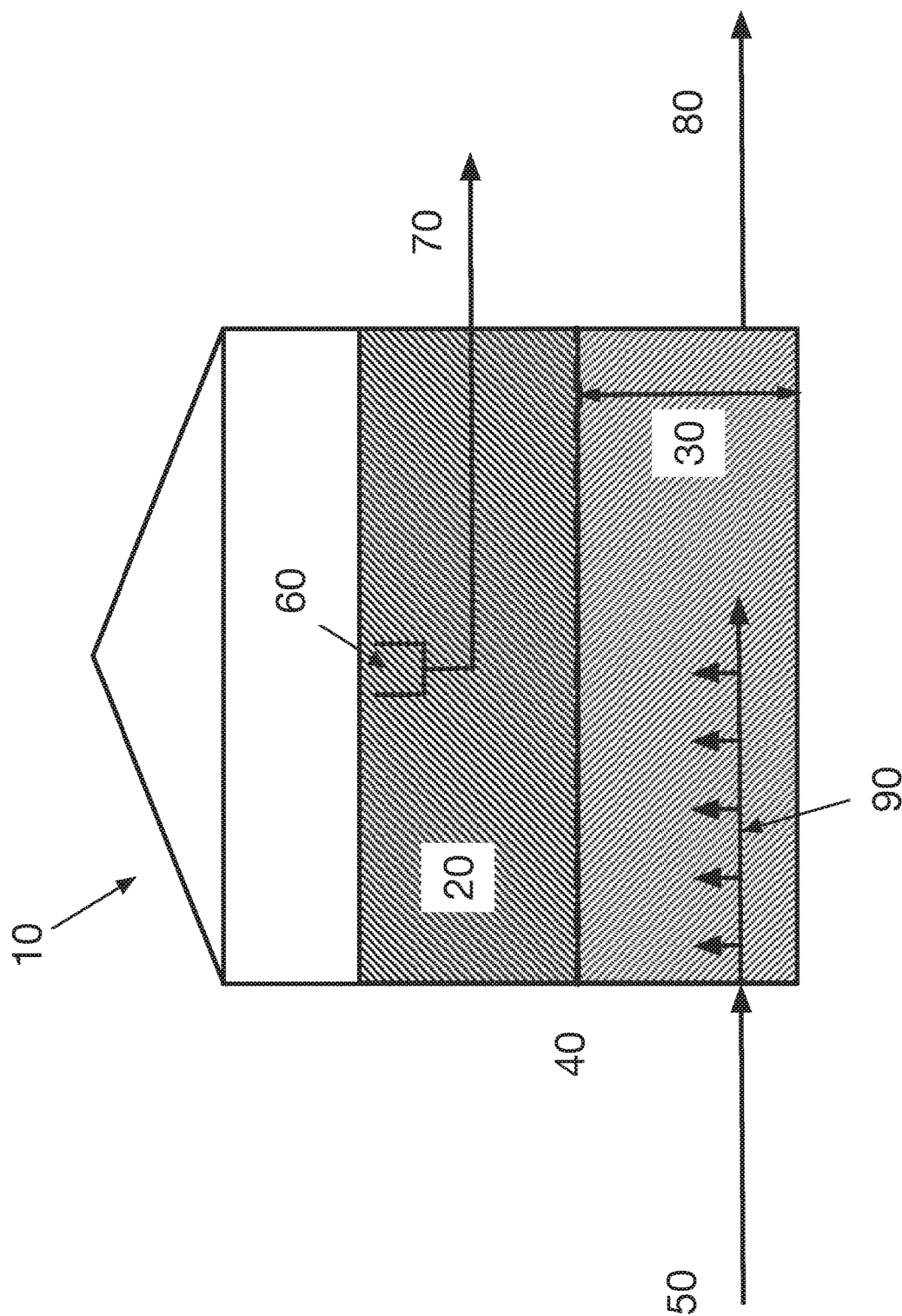
FIG. 1 depicts an embodiment of the invention.

The invention provides a method of reducing the salt content of a neutralized aralkyl hydroperoxide cleavage mass stream before it is passed to a crude purification column and further purification columns to recover the phenol and acetone. The neutralized aralkyl (aryl alkyl or alkyl aryl) hydroperoxide cleavage mass stream may be passed to one or more wash/separation steps to remove a portion of the neutralization salts, in a similar fashion to that described in U.S. Pat. No. 6,965,056. Even with the wash step, there is still an amount of neutralization salts that will foul the crude purification column with deposits of salt on the column trays and other downstream equipment.

The neutralized aralkyl hydroperoxide cleavage mass stream, hereinafter referred to as the neutralized stream, may optionally be passed to one or more coolers that result in a reduced temperature neutralized stream. The coolers may use indirect heat exchange, such as shell and tube heat exchangers or air coolers, to reduce the temperature of the neutralized stream. In another embodiment, the neutralized stream may be heated.

The neutralized stream is then fed into a vessel. The vessel has at least one inlet for the neutralized stream, and at least two outlets. The vessel is preferably large enough to provide surge capacity for the process. In the vessel, the neutralized stream separates into two phases, an aqueous phase and a hydrocarbon phase, due to the slight density differences between the two phases. The hydrocarbon layer is less dense than the aqueous layer. Due to the density differences, a salt concentration gradient forms. The salt concentration gradient results in a lower concentration of salt in the hydrocarbon layer.

The inlet for the neutralized stream may be positioned in the vessel such that the neutralized stream enters the vessel in the aqueous layer. The inlet may be at the bottom of the vessel or near the bottom of the vessel.

The inlet may include a diffuser or sparger through which the neutralized stream is fed into the vessel. This allows the neutralized stream to be fed at several locations throughout the aqueous layer which results in reduced turbulence as the neutralized stream enters the aqueous layer at a lower velocity. Any means known to one of ordinary skill in the art including baffles or other devices to disperse and/or slow the flow rate of the neutralized stream as it enters the vessel can be used. By reducing the turbulence caused at the inlet, the interface between the hydrocarbon layer and the aqueous layer is more easily maintained.

As described above, the aqueous layer forms below the hydrocarbon layer in the vessel. The amount of the aqueous layer in the vessel is controlled by withdrawing an aqueous stream through the second outlet. As more of the aqueous stream is removed, the level of the aqueous layer will be lowered. This provides for control of the aqueous layer and the interface level between the aqueous layer and the hydrocarbon layer.

A hydrocarbon stream is withdrawn from the vessel through the first outlet. This hydrocarbon stream contains a large amount of the phenol and acetone that was produced in the cleavage step. This hydrocarbon stream is passed to the crude purification column and then to subsequent purification columns and other downstream steps.

The first outlet is preferably located vertically above the first inlet. The neutralized stream is thus fed into the vessel at a lower level than the outlet for the hydrocarbon stream.

In one embodiment, the first outlet is a floating suction where the outlet is maintained at or near the top of the hydrocarbon layer. This provides the maximum distance between the inlet and the outlet. There is a gradient of salt concentration throughout the hydrocarbon layer and the salt concentration is lower towards the top of the hydrocarbon layer. Therefore, a floating suction provides for a reduced salt concentration in the hydrocarbon stream that is passed to the downstream equipment.

In another embodiment, the first outlet is a fixed outlet positioned at a level towards the top of the typical hydrocarbon layer level in the vessel. In this embodiment, additional outlets may be positioned at other levels in the vessel so that there is always an outlet that is located near the top of the hydrocarbon layer. As the top of the hydrocarbon layer changes, there will always be an outlet that is located at or near the top of the hydrocarbon layer to provide a hydrocarbon stream with a reduced salt concentration.

In one embodiment, an aqueous stream may be added to the neutralized stream. This aqueous stream may be added before the neutralized stream enters the vessel or the aqueous stream may be added directly to the vessel. In another embodiment, the aqueous stream that exits the vessel through the second outlet may be recirculated to the vessel, either by adding it to the neutralized stream before it enters the vessel or by returning the aqueous stream directly to the vessel. In one embodiment, the level of the aqueous layer in the vessel is kept as low as possible.

FIG. 1 depicts an embodiment of the invention that will be described in more detail below. FIG. 1 depicts a vessel, tank 10 that has an inlet 50 that comprises a flow diffuser 90. The neutralized stream is passed through the inlet 50 and flow diffuser 90 into the tank 10. The flow diffuser reduces the flow rate of the neutralized stream to maintain an intact interface between hydrocarbon layer 20 and aqueous layer 30. The hydrocarbon stream is removed via outlet 70. In this embodiment, outlet 70 comprises a floating suction 60. The hydrocarbon portion of the neutralized stream makes its way from the flow diffuser through the aqueous layer 30 and into the hydrocarbon layer 20. The hydrocarbon portion that is withdrawn via outlet 70 has a reduced salt concentration relative to the salt concentration of the neutralized stream. The aqueous stream is removed via outlet 80 to maintain a desired amount of the aqueous layer in the tank 10. This desired amount can be controlled by an interface level controller 40.

FIG. 2 depicts another embodiment of the invention that will be described in more detail below. FIG. 2 depicts a vessel, tank 110 that has an inlet 150 that comprises a flow diffuser 190. The neutralized stream is passed through the inlet 150 and flow diffuser 190 into the tank 110. The flow diffuser reduces the flow rate of the neutralized stream to maintain an intact interface between hydrocarbon layer 120 and aqueous layer 130. The hydrocarbon stream is removed via outlet 170. In this embodiment, outlet 170 is connected to three fixed suctions 160. The hydrocarbon portion of the neutralized stream makes its way from the flow diffuser through the aqueous layer 130 and into the hydrocarbon layer 120. The hydrocarbon portion that is withdrawn via outlet 170 has a reduced salt concentration relative to the salt concentration of the neutralized stream. The specific outlet 160 that is used is determined based on the level of the hydrocarbon layer 120 such that the hydrocarbon is removed at or near the top of the hydrocarbon layer 120. The aqueous stream is removed via outlet 180 to maintain a desired amount of the aqueous layer in the tank 110. This desired amount can be controlled by an interface level controller 140.

In one embodiment, the invention provides retrofitting an existing vessel with an outlet located at or near the top of the typical hydrocarbon layer level. This outlet may be a floating suction or it may be a fixed suction that is located above the inlet to the vessel.

EXAMPLES

Example 1

In this example, two sets of samples were taken from a vessel containing a neutralized aralkyl hydroperoxide cleavage mass stream. The first set of samples were taken near the top of the liquid level in the vessel, and the second set of samples were taken near the middle of the liquid level in the vessel. The results from the sodium analysis by ion chromatography are shown in Table 1. The results show that the samples taken near the top of the vessel had approximately half as much sodium as the samples taken near the middle portion of the vessel.

TABLE 1

| Sample | Top #1 | Top #2 | Top #3 | Mid #1 | Mid #2 | Mid #3 |
|---|---|---|---|---|---|---|
| Na (ppmw) | 8.6 | 8.4 | 14.6 | 17.6 | 15 | 15.7 |

Example 2

In this example, samples of a neutralized aralkyl hydroperoxide cleavage mass stream were maintained at 22° C. or 50° C. for 4 hours. Some of the samples were agitated and others were left idle. The salt concentration was tested at the sampling depth shown in the Table 2 (with the sampling depth defined as the height the sample was taken where 0% is the bottom of the vessel and 100% is the top of the vessel). The details of each experiment and the resulting salt concentration are shown in Table 2. Agitation of the samples resulted in a more uniform distribution of the salt, although the salt was still lower for samples 1 and 2 as compared to samples 3 and 4. A significant difference is shown in the non-agitated samples where the salt concentration in samples 5 and 6 is about twenty times lower than the salt concentration of samples 7 and 8. Samples 9 and 10 show similar results at an elevated temperature.

TABLE 2

| Sample | Temperature | Agitation | Sampling Depth | Na (ppmw) |
|--------|-------------|-----------|----------------|-----------|
| 1      | 22° C.      | Y         | 85%            | 30.51     |
| 2      | 22° C.      | Y         | 85%            | 29.41     |
| 3      | 22° C.      | Y         | 16%            | 39.72     |
| 4      | 22° C.      | Y         | 16%            | 33.41     |
| 5      | 22° C.      | N         | 89%            | 8.74      |
| 6      | 22° C.      | N         | 89%            | 8.16      |
| 7      | 22° C.      | N         | 17%            | 159.52    |
| 8      | 22° C.      | N         | 17%            | 161.8     |
| 9      | 50° C.      | N         | 79%            | 7.22      |
| 10     | 50° C.      | N         | 16%            | 99.16     |

That which is claimed is:

1. A method of reducing the salt content of a neutralized aralkyl hydroperoxide cleavage mass stream comprising passing the neutralized stream into a vessel, the vessel having an inlet, two outlets, an aqueous layer and a hydrocarbon layer wherein the neutralized stream enters the vessel through a first inlet and a hydrocarbon stream exits the vessel through a first outlet that is in fluid communication with the hydrocarbon layer.

2. The method of claim 1 wherein the neutralized aralkyl hydroperoxide cleavage mass stream comprises one or more of phenol, acetone, alpha-methyl styrene, cumene, cumyl phenol, dimethylbenzyl alcohol, acetophenone, alpha-methyl styrene dimers, tars, heavies.

3. The method of claim 2 wherein the neutralized aralkyl hydroperoxide cleavage mass stream further comprises salts produced in a neutralization step.

4. The method of claim 1 wherein the hydrocarbon layer is less dense than the aqueous layer.

5. The method of claim 1 wherein the first inlet is in fluid communication with the aqueous layer.

6. The method of claim 1 wherein the first inlet is a diffuser with a plurality of openings to allow the neutralized stream to enter the vessel at a plurality of locations.

7. The method of claim 1 wherein the second outlet is in fluid communication with the aqueous layer.

8. The method of claim 1 wherein the first outlet is located vertically above the first inlet.

9. The method of claim 1 wherein the first outlet is a floating suction that is positioned at or near the top of the hydrocarbon layer.

10. The method of claim 1 wherein the first outlet is located on a wall of the vessel.

11. The method of claim 10 further comprising controlling the level in the vessel such that the first outlet is in fluid communication with the hydrocarbon layer.

12. The method of claim 11 wherein the vessel further comprises additional outlets at lower levels that can be used as outlets for the hydrocarbon stream.

13. The method of claim 12 wherein one additional outlet is positioned between the top of the hydrocarbon layer and the interface between the hydrocarbon layer and the aqueous layer.

14. The method of claim 12 wherein one additional outlet is positioned at or near the interface between the hydrocarbon layer and the aqueous layer.

15. The method of claim 1 further comprising controlling the level of the interface between the hydrocarbon layer and the aqueous layer.

16. The method of claim 15 wherein the level of the interface is controlled by controlling the flow through the second outlet.

17. The method of claim 1 wherein the neutralized stream enters the vessel, passes through the aqueous layer and at least a portion of the stream passes into the hydrocarbon layer.

18. The method of claim 17 wherein the portion of the neutralized stream that passes into the hydrocarbon layer has a lower salt content than the neutralized stream that enters the vessel.

19. The method of claim 1 further comprising cooling or heating the neutralized aralkyl hydroperoxide cleavage mass stream before it enters the first inlet into the vessel.

20. The method of claim 1 further comprising adding an aqueous stream to the neutralized aralkyl hydroperoxide cleavage mass stream.

21. The method of claim 1 wherein an aqueous stream is recirculated from the vessel to be combined with the neutralized aralkyl hydroperoxide cleavage mass stream.

22. The method of claim 1 further comprising washing the neutralized aralkyl hydroperoxide cleavage mass stream in a wash step and/or washing the hydrocarbon stream that exits the vessel through the first outlet.

* * * * *